United States Patent [19]

Motegi et al.

[11] Patent Number: 5,059,707

[45] Date of Patent: Oct. 22, 1991

[54] HYDROXYL GROUP-CONTAINING ORGANOSILICON COMPOUND

[75] Inventors: Hisao Motegi; Takeshi Sunaga; Michio Zenbayashi, all of Gunma, Japan

[73] Assignee: Toshiba Silicone Co., Ltd., Tokyo, Japan

[21] Appl. No.: 499,875

[22] Filed: Mar. 27, 1990

[30] Foreign Application Priority Data

Mar. 29, 1989 [JP] Japan .................................. 1-76912

[51] Int. Cl.$^5$ .................................. C07F 7/08
[52] U.S. Cl. .................................. 556/449
[58] Field of Search .......................... 556/449

[56] References Cited

U.S. PATENT DOCUMENTS

| | | | |
|---|---|---|---|
| 3,355,473 | 11/1967 | Clark et al. | 556/449 X |
| 3,976,676 | 8/1976 | Lohse et al. | 556/449 |
| 4,013,698 | 3/1977 | Lohse et al. | 556/449 X |
| 4,839,443 | 6/1989 | Akutsu et al. | |

FOREIGN PATENT DOCUMENTS

| | | |
|---|---|---|
| 10294525 | of 0000 | European Pat. Off. . |
| 20266895 | of 0000 | European Pat. Off. . |
| 62-195389 | of 0000 | Japan . |
| 1088493 | of 0000 | United Kingdom . |

*Primary Examiner*—Paul F. Shaver
*Attorney, Agent, or Firm*—Sughrue, Mion, Zinn, Macpeak & Seas

[57] ABSTRACT

A hydroxyl group-containing organosilicon compound represented by formula (I)

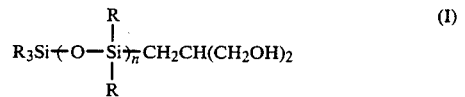

wherein R which may be the same or different each represents an alkyl group, an aryl group, or an alkenyl group, and n is 0 or an integer of 1 to 1,000. The compound can be suitably used for modification of surface properties of synthetic resins.

4 Claims, No Drawings

HYDROXYL GROUP-CONTAINING ORGANOSILICON COMPOUND

FIELD OF THE INVENTION

The present invention relates to an organosilicon compound useful for modifying properties of synthetic resins. More particularly, this invention relates to a novel hydroxyl group-containing organosilicon compound useful for the modification of surface properties of synthetic resins such as polyurethanes, polyesters, and the like produced by utilizing the reactivity of polyols.

BACKGROUND OF THE INVENTION

Conventionally known organosilicon compounds for use in the modification of surface properties of polyurethanes or polyesters include compounds of formulas (1), (2) and (3), having a hydroxyl group or an organic group having a hydroxyl group at both ends of polydimethylsiloxane, and compounds of formula (4) having an organic group having two hydroxyl groups different in reactivity at one end of polydimethylsiloxane.

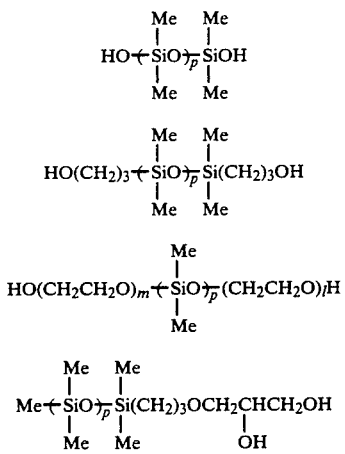

wherein Me represents a methyl group, and l, m and p each represents a positive integer.

However, modification of a polymer by the siloxane compound having a hydroxyl group at both ends thereof has the following problem. That is, since the whole siloxane segment is introduced into the resulting polymer, the siloxane compound should be used in a considerably large proportion for attaining sufficient modification of surface properties of the final resin molded articles.

The above problem is overcome with the compound of formula (4) as disclosed in, for example, JP-A-62-195389. (The term "JP-A" as used herein means an "unexamined published Japanese patent application".) However, the two hydroxyl groups of this compound greatly differ from each other in reactivity because the compound has a structure in which one of the two hydroxyl groups is bonded to a primary carbon atom and the other is bonded to a secondary carbon atom. For this reason, when this compound is used, not only do copolymerization reactions proceed with difficulty but there is another problem that a polymer having the intended molecular structure cannot be obtained.

SUMMARY OF THE INVENTION

Accordingly, an object of the present invention is to provide a novel hydroxyl group-containing organosilicon compound which is free from the above problems and is useful in the modification of surface properties of polyurethanes, polyesters, and other resins.

The hydroxyl group-containing organosilicon compound of the present invention is represented by formula (I)

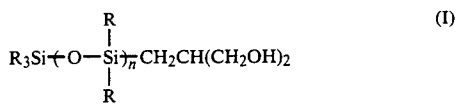

wherein R which may be the same or different each represents an alkyl group, an aryl group, or an alkenyl group, and n is 0 or an integer of 1 to 1,000.

DETAILED DESCRIPTION OF THE INVENTION

The compound of the formula (1) is hereinafter referred to as compound (1).

In the compound (I) of this invention, R is an alkyl group, an aryl group, or an alkenyl group. Examples of the alkyl group include methyl, ethyl, propyl, butyl, pentyl, hexyl, and dodecyl, examples of the aryl group include phenyl and tolyl, and examples of the alkenyl group include vinyl and allyl. Of these, alkyl groups having 1 to 4 carbon atoms are preferred, with methyl being particularly preferred, from the standpoints of easy availability of raw materials and easy synthesis of the compounds.

n is 0 or an integer of 1 to 1,000, preferably 1 to 200. If n is larger than 1,000, not only does the viscosity of the compound become so high that the compound is difficult to handle, but synthesis thereof is difficult to control.

One example of a process for producing the compound (I) of the present invention is briefly explained below.

First, 2-methylene-1,3-propanediol (II) is reacted with hexamethyldisilazane (III) in the presence of a catalytic amount of ammonium chloride to synthesize 2-methylene-1,3-bis(trimethylsiloxy)propane (IV). This compound (IV) is then subjected to an addition reaction with a one-end-hydrogenated diorganosiloxane (V) in the presence of a catalyst such as a platinum compound to give a diorganosiloxane derivative (VI). This derivative (VI) is subjected to a detrimethylsilylation reaction to remove the trimethylsilyl groups, thereby to obtain the compound (I) of the invention. The above process is illustrated by the following reaction formulas.

(II)      (III)

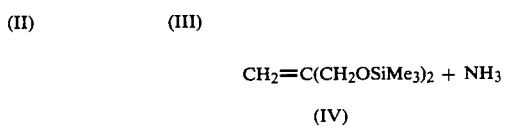
(IV)

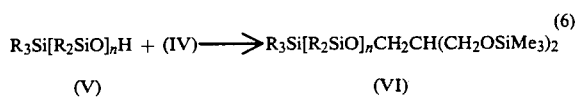
(V)      (VI)

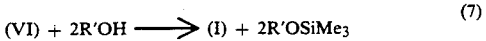

wherein R and n are the same as defined above, and R' represents an alkyl group.

Compound (II) can be obtained, for example, by a method in which 5-norbornen-2-ylidene dimethanol is subjected to a retro Diels-Alder reaction (E. J. Corey, J. W. Suggs; Tetrahedron Lett., 44, 3775-3778(1975)) or a method in which -chloro-2-chloromethylpropene is esterified with acetic acid to synthesize 2-methylene-1,3-propanediol diacetate, which is then subjected to an ester interchange reaction with methanol Y. Ducharme, S. Latour, J. D. Wuest; Organometallics, 3, 08-211(1984)).

The one-end-hydrogenated diorganosiloxane (V) can be obtained as follows. A compound of formula (V) in which n is 0, i.e., a triorganosilane, can be easily obtained by reacting a triorganochlorosilane of the formula $R_3SiCl$ (wherein R is the same as defined above) with a theoretical molar amount of lithium aluminum hydride in ether. A compound of formula (V) in which n is 1, i.e., a 1,1,3,3,3-pentaorganodisiloxane, can be easily obtained, for example, by subjecting a triorganochlorosilane of the formula $R_3SiCl$ (wherein R is the same as defined above) and a diorganochlorosilane of the formula $R_2HSiCl$ (wherein R is the same as defined above) to a cohydrolysis reaction. A compound of formula (V) in which n is 2 or larger can be obtained by polymerizing a hexaorganocyclotrisiloxane of the formula $[R_2SiO]_3$ in tetrahydrofuran in the presence of an organolithium compound of the formula RLi (wherein R is the same as defined above), and then subjecting the resulting polymer to a desalting reaction with a diorganochlorosilane of the formula $R_2HSiCl$ (wherein R is the same as defined above) (for example, Y. Tezuka, A. Fukushima, K. Imai; Makromolekulare Chemie, 186, 685(1985)).

The reaction shown by reaction formula (5) above is a trimethylsilylation reaction in which the hydroxyl groups are replaced by trimethylsilyl groups by means of hexamethyldisilazane. This reaction can be carried out according to conventional methods.

In conducting the addition reaction of compound (V) with compound (IV) as shown by reaction formula (6), the compound (IV) is used in an amount of 1 mole or more, preferably 1.1 moles or more, per mole of the compound (V). Catalysts for this addition reaction are complex compounds of Group VIII elements in the periodic table. Of these, a platinum compound prepared by dissolving chloroplatinic acid in an alcohol or a carbonyl compound, and complex compounds of various olefins with platinum or rhodium are preferably used.

The detrimethylsilylation reaction of compound (VI), as shown by reaction formula (7), can be conducted using a lower alcohol of the formula R'OH (wherein R' is the same as defined above), preferably methanol or ethanol. For example, a stoichiometrically large excess of methanol is added to compound (VI) and the resulting mixture is heated for several hours with refluxing, whereby the compound (I) of this invention can be obtained.

By using the compound of the present invention as one of the comonomers for a polyurethane, a polyester, or the like, a polymer can be obtained which has a structure in which siloxane chains are attached as pendant groups to the amine chain.

Due to the compound of the present invention, the polymer thus obtained possesses properties such as heat resistance, water repellency, non-fouling properties, non-adhesive characteristics, flexibility, wear resistance, and gas permeability, which are the inherent characteristics of the siloxane compounds, and hence the thus-modified polymer is useful as a medical material, a fiber-modifying material, etc.

The present invention will be explained in more detail by reference to the following Examples, which should not be construed to be limiting the scope of the invention. In the Examples, all parts are by weight.

EXAMPLE 1

Into a flask equipped with a stirrer, thermometer, dropping funnel, reflux condenser, and oil bath were introduced 0.06 part of a solution prepared by dissolving 0.5 part of chloroplatinic acid in 25 parts of isopropanol, and 53.4 parts of 2-methylene-1,3- bis(-trimethylsiloxy)propane. Stirring was then initiated and the liquid in the flask was heated to 70° C.

29.6 Parts of 1,1,3,3,3-pentamethyldisiloxane was added dropwise to the flask from the dropping funnel over a period of 15 minutes, while appropriately cooling the liquid reaction mixture to maintain the liquid temperature at 80°-90° C. After completion of the addition, stirring was continued for 1 hour at a liquid temperature of 90° C. Upon analysis by gas chromatography, it was ascertained that the peak due to 1,1,3,3,3-pentamethyldisiloxane had disappeared.

After the reaction mixture was allowed to cool, a fraction having a boiling point of 96°-98° C./3 Torr was taken by vacuum distillation, thereby obtaining 68.4 parts of 1-(2-trimethylsiloxymethyl-3-trimethylsiloxypropyl)-1,1,3,3,3-pentamethyldisiloxane in a colorless, transparent liquid state (yield 90%). As a result of analysis by gas chromatography, the purity of this product was found to be 97%.

The above-obtained product was subjected to elementary analysis, infrared spectroscopic analysis, :H nuclear magnetic resonance (:H NMR) analysis, and mass spectrometric analysis. The results obtained are shown below. From those analyses, the product was ascertained to have the following molecular structure.

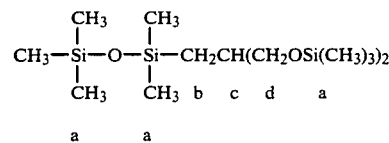

Elementary analysis:
Calculated value! Si; 29.50%, C; 47.31%, H; 10.59%, 0; 12.60%.
Found value [Si; 29.51%, C; 47.30%, H; 10.57%, 0; 12.62%.

Infrared spectroscopic analysis (liquid film method):

| Infrared spectroscopic analysis (liquid film method): | |
| --- | --- |
| Wave number (cm$^{-1}$) | Assignment |
| 2940 | C—H |
| 1100-1020 | Si—O |

| $^1$H NMR analysis (in CDCl$_3$): | | | |
| --- | --- | --- | --- |
| Position | Chemical shift δ (ppm) | Number of hydrogen atoms | Multiplicity |
| a | −0.01 | 33 | s |
| b | 0.25–0.45 | 2 | m |
| c | 1.6–1.8 | 1 | m |

| | -continued | | |
|---|---|---|---|
| d | 3.4 | 4 | d |

Mass spectrometric analysis (m/e): 380 (M+)

38.0 Parts of the above-obtained 1-(2-trimethylsiloxymethyl-3-trimethylsiloxypropyl) -1,1,3,3,3pentamethyldisiloxane and 375 parts of methanol were introduced into the same type of a flask as used above, and the resulting mixture was heated with refluxing for 2 hours. After the reaction mixture was allowed to cool, a fraction having a boiling point of 133°–136° C./6 Torr was taken by vacuum distillation, thereby obtaining 21.0 parts of 1-(2-hydroxymethyl-3-hydroxypropyl)-1,1,3,3,3- pentamethyldisiloxa in a colorless, transparent liquid state (yield 89%). Upon analysis by gas chromatography, the purity of this product was found to be 95%.

The above-obtained product was subjected to elementary analysis, infrared spectroscopic analysis, $^1$H NMR analysis, and mass spectrometric analysis. The results obtained are shown below. From those analyses, the product was ascertained to have the following molecular structure.

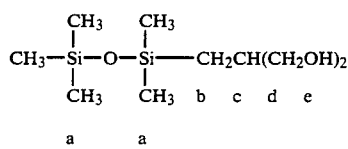

Elementary analysis:
Calculated value: Si; 23.76%, C; 45.71%, H; 10.23%, O; 20.30%.
Found value: Si; 23.78%, C; 45.69% H; 10.22%, O; 10.31%

| Infrared spectroscopic analysis (liquid film method): | |
|---|---|
| Wave number (cm$^{-1}$) | Assignment |
| 3500–3200 | O—H |
| 2950 | C—H |
| 1100–1000 | Si—O |

| $^1$H NMR analysis (in CDCl$_3$): | | | |
|---|---|---|---|
| Position | Chemical shift δ (ppm) | Number of hydrogen atoms | Multiplicity |
| a | 0.03 | 15 | s |
| b | 0.2–0.4 | 2 | d |
| c | 1.8–2.0 | 1 | m |
| d | 3.5 | 4 | d |
| e | 4.25 | 2 | bs |

Mass spectrometric analysis (m/e): 236 (M+)

EXAMPLE 2

Reaction of 2-methylene-1,3-bis(trimethylsiloxy)-propane was conducted in the same manner as in Example 1 except that 7.0 parts of the compound was reacted with 84 parts of one-end-hydrogenated polydimethylsiloxane (hydrogen equivalent: 4,200, i.e., number average molecular weight: 4,200) in place of 1,1,3,3,3-pentamethyldisiloxane used in Example 1. After completion of the reaction, the reaction mixture was analyzed by infrared spectroscopy and it was ascertained that the absorption peak (2,140 cm$^{-1}$) the Si-H group had disappeared. From the resulting reaction mixture, low boiling point fractions including raw materials remaining unreacted were removed under conditions of 120° C./1 Torr over 2 hours. To this distillation residue was then added 250 parts of methanol, and the resulting mixture was heated for 3 hours with refluxing. Thereafter, excess methanol and low boiling point by-products were removed under conditions of 70° C./3 Torr over 2 hours. Thus, 86.0 parts of one-end-dihydroxylated polydimethylsiloxane in a colorless, transparent liquid state was obtained as the distillation residue (yield 97%).

The above-obtained product was subjected to infrared spectroscopic analysis, $^1$H NMR analysis, hydroxy equilvalent determination, and GPC analysis. The results obtained are shown below. From those analyses, the product was ascertained to have the following molecular structure.

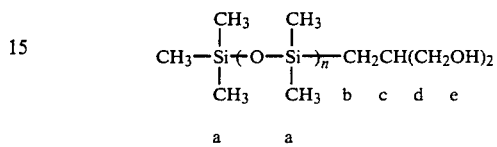

| Infrared spectroscopic analysis (liquid film method): | |
|---|---|
| Wave number (cm$^{-1}$) | Assignment |
| 3500–3200 | O—H |
| 2950 | C—H |
| 1100–1000 | Si—O |

| $^1$H NMR analysis (in CDCl$_3$): | | | |
|---|---|---|---|
| Position | Chemical shift δ (ppm) | Number of hydrogen atoms | Multiplicity |
| a | 0.03 | — | s |
| b | 0.2–0.4 | 2 | d |
| c | 1.8–2.0 | 1 | m |
| d | 3.5 | 4 | d |
| e | 4.25 | 2 | bs |

Hydroxy equivalent determination
Hydroxy equivalent 2,100
GPC analysis
Weight-average molecular weight expressed in terms of polystyrene (M$_w$) 4,900
Number-average molecular weight expressed in terms of polystyrene (M$_n$) 4,500
Degree of polydispersion (M$_w$/M$_n$) 1.09.

While the invention has been described in detail and with reference to specific embodiments thereof, it will be apparent to be skilled in the art that various changes and modifications can be made therein without departing from the spirit and scope thereof.

What is claimed is:

1. A hydroxyl group-containing organosilicon compound represented by formula (I)

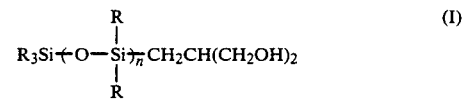

wherein R which may be the same or different each represents an alkyl group, an aryl group, or an alkenyl group, and n is an integer of 1 to 1,000.

2. A hydroxyl group-containing organosilicon compound as claimed in claim 1, wherein R is an alkyl group having 1 to 4 carbon atoms.

3. A hydroxyl group-containing organosilicon compound as claimed in claim 1, wherein R is methyl.

4. A hydroxyl group-containing organosilicon compound as claimed in claim 1, wherein n is an integer of 1 to 200.

* * * * *